(12) United States Patent
Sun et al.

(10) Patent No.: US 7,144,980 B2
(45) Date of Patent: Dec. 5, 2006

(54) MANUFACTURE OF WEB SUPERABSORBENT POLYMER AND FIBER

(75) Inventors: Fang Sun, Lisle, IL (US); Bernfried A. Messner, Greensboro, NC (US)

(73) Assignee: Stockhausen GmbH, Krefeld (DE)

( * ) Notice: Subject to any disclaimer, the term of this patent is extended or adjusted under 35 U.S.C. 154(b) by 0 days.

(21) Appl. No.: 11/052,331

(22) Filed: Feb. 7, 2005

(65) Prior Publication Data

US 2005/0131367 A1   Jun. 16, 2005

Related U.S. Application Data

(62) Division of application No. 09/603,323, filed on Jun. 26, 2000.

(60) Provisional application No. 60/141,411, filed on Jun. 29, 1999.

(51) Int. Cl.
*C08F 6/00* (2006.01)
(52) U.S. Cl. .................. 528/480; 428/402; 604/368
(58) Field of Classification Search ............... 428/402; 528/480; 604/368
See application file for complete search history.

(56) References Cited

U.S. PATENT DOCUMENTS

| | | | | |
|---|---|---|---|---|
| 5,409,771 A | * | 4/1995 | Dahmen et al. | 428/327 |
| 6,136,873 A | * | 10/2000 | Hahnle et al. | 521/62 |
| 6,174,929 B1 | * | 1/2001 | Hahnle et al. | 521/64 |

OTHER PUBLICATIONS

International Search Report mailed on Oct. 17, 2000 in PCT/IB00/00867.
International Preliminary Examination Report mailed on Sep. 25, 2001 in PCT/IB00/00867.
European Examination Communication mailed on Apr. 11, 2003 in EP 00 938 962.8-2123.

* cited by examiner

*Primary Examiner*—Terressa Boykin
(74) *Attorney, Agent, or Firm*—Smith Moore LLP

(57) ABSTRACT

A web of superabsorbent polymer and fiber made by an in situ neutralization, wet-laid process, wherein the degree of neutralization of the superabsorbent polymer is partial, preferably less than about 80 mol %. The web exhibits an excellent centrifuge retention capacity property, as compared to prior webs of superabsorbent polymer and cellulosic fiber made by in situ neutralization, wherein the degree of neutralization is total, such as 100 mol % or more.

13 Claims, No Drawings

MANUFACTURE OF WEB SUPERABSORBENT POLYMER AND FIBER

This is a Utility Application that is a divisional of patent application Ser. No. 09/603,323, filed Jun. 26, 2000, now pending, that claims priority to U.S. Provisional Application Ser. No. 60/141,411 filed Jun. 29, 1999.

TECHNICAL FIELD

The present invention relates, in general, to wet-laid webs of superabsorbent polymer and fiber. More particularly, the present invention relates to such webs that are in situneutralized, wet-laid webs, and even more particularly, partially in situ neutralized, wet-laid webs. By in situ neutralization is meant that the neutralization of polymer to make it into a superabsorbent polymer is conducted after mixing the polymer with fiber during the wet-laid process of making a web, as opposed to a wet-laid process of making a web where already neutralized superabsorbent polymer is mixed with fiber. As is well known, webs have many uses, especially in disposable sanitary articles, such as diapers, and adult incontinence garments. The partially in situ neutralized, wet-laid web of the present invention exhibits a superior centrifuge retention capacity property, as compared to prior art, totally in situ neutralized, wet-laid webs, and consequently, the inventive webs are especially useful in disposable sanitary articles.

DEFINITIONS OF ABBREVIATIONS

| Abbreviations | Definitions |
| --- | --- |
| AUL | absorbency under load |
| All-PEGMA | allyloxy polyethylene glycol methacrylate, a X-linking agent |
| cm | centimeter |
| CRC | centrifuge retention capacity |
| X-linking | cross-linking |
| EO-TMPTA | ethoxylated trimethylol-propane triacrylate, a X-linking agent |
| g | gram |
| mg | milligram |
| mm | millimeter |
| n.a. | not applicable |
| pre-SAP | a polymer which may absorb a minor amount of water or may be non-water absorbent, and which is capable upon neutralization of becoming a SAP |
| psi | pounds per square inch |
| SAP | superabsorbent polymer, a polymer which absorbs over 50 times, more preferably over 75 times, even more preferably over 100 times, its weight in water |

BACKGROUND OF THE INVENTION

The primary consideration, with early development of superabsorbent technology, was that superabsorbent polymers exhibit a high swelling capacity on contact with liquid i.e., water, body fluids, etc. Later, as technology was developed to mix superabsorbent polymers with fiber to make a web, typically for use in disposable sanitary articles (for instance, diapers, incontinence garments, sanitary napkins, and bandages), consideration shifted to problems with the mechanical load caused by movement of the person wearing the sanitary article.

Hence, in addition to research focusing on superabsorbent polymers having a high swelling capacity, research focused on superabsorbent polymers also having a high capability for retaining liquid when pressure was applied. This led to the development of a way to measure the capability in accordance with two tests, namely the test for centrifuge retention capacity (CRC) and the test for absorbency under load (AUL). Published European Patent Application No. 0 339 461 A1 (published Nov. 2, 1989; priority to U.S. patent application Ser. No. 184,302 (Parent) and U.S. patent application Ser. No. 334,260 (Continuation-in-Part), which Continuation-in-Part has issued as U.S. Pat. No. 5,147,343) to Kellenberger, assignor to Kimberly-Clark Corporation, contains an excellent discussion of the test for AUL.

Although as is well known, webs typically are made by mixing superabsorbent polymer and fiber in either an air-laid process or a wet-laid process, research continues for improved ways to make a web. For instance, one variation of a wet-laid process is disclosed in U.S. Pat. No. 4,270,977 (issued Jun. 2, 1981) to Herman and Kruse, assignors to NL Industries, Inc. More specifically, this patent describes a wet-laid process for making a web of superabsorbent polymer and fiber, in which polymer that is not superabsorbent polymer, but is capable of becoming superabsorbent polymer upon neutralization, is admixed with fiber, and then, totally in situ neutralized (i.e., the in situ neutralization of the polymer to convert it into the superabsorbent polymer is to a degree of 100 to 120 mol %) to create the web. As discussed in the patent to Herman and Kruse, in situ neutralization uses less water, as compared to conventional wet-laid processes of mixing superabsorbent polymer with fiber. Hence, in situ neutralization is more cost effective for a large-scale factory production.

General background with respect to various superabsorbent polymers, their methods of manufacture, and their uses can be seen in Buchholz, "Keeping Dry with Superabsorbent Polymers", Chemtech, September, 1994. Also, a good discussion of the methods for making superabsorbent polymers can be seen in U.S. Pat. No. 5,409,771 (issued Apr. 25, 1995) to Dahmen and Mertens, assignors to Chemische Fabrik Stockhausen GmbH. As discussed in the journal article by Buchholz and in the patent to Dahmen and Mertens, superabsorbent polymers are made by two methods, one being the solvent polymerization technique and the other being the inverse suspension or emulsion polymerization technique.

Both techniques typically begin with an aqueous monomer solution, for instance of acrylic acid, which is neutralized at some point. With solvent polymerization, the acid solution also contains a multi-functional network cross-linking agent, and is converted into a gel by radical polymerization. The gel is dried, ground, and screened to a suitable particulate size. In contrast, with inverse suspension or emulsion polymerization, the acid solution is dispersed in a hydrophobic organic solvent by employing colloids or emulsifiers. Next, polymerization is initiated with radical initiators. After completion of polymerization, water is azeotropically removed from the reaction mixture, and the product is then filtered and dried. Network cross-linking typically is accomplished by dissolving a poly-functional network cross-linking agent in the monomer solution.

The disclosures of the above-mentioned patents and published patent application are incorporated herein by reference.

BRIEF SUMMARY AND OBJECTS OF THE INVENTION

Accordingly, the present invention provides a water sorptive product which is a partially in situ neutralized, wet-laid web of superabsorbent polymer and fiber, wherein the product, as compared to a totally in situ neutralized wet-laid web, exhibits a superior centrifuge retention capacity property. Preferably, the superabsorbent polymer has a partial neutralization to a degree less than about 80 mol %.

Also, the present invention provides a method to improve the centrifuge retention capacity property of in situ wet-laid webs, wherein the method comprises admixing in water a potentially water swellable polymer (i.e., a polymer referred to herein as a pre-SAP) component with a fibrous component, followed by contacting the mixture with a neutralizing agent in order partially to neutralize the polymer component (preferably, partially to a degree of neutralization less than about 80 mol %), and achieving a web of a superabsorbent polymer (referred to herein as a SAP) component with a fibrous component, wherein the web has a superior centrifuge retention capacity property, as compared to a totally in situ neutralized wet-laid web.

Hence, it is an object of the invention to provide an in situ neutralized wet-laid web with liquid retention properties superior to those of prior art in situ neutralized wet-laid webs.

It is a further object of the present invention to provide a method to improve the liquid retention properties of in situ neutralized wet-laid webs.

Some of the objects of the invention having been stated above, other objects will become evident as the description proceeds, when taken in connection with the accompanying Laboratory Examples as best described below.

DETAILED DESCRIPTION OF THE INVENTION

As long as the above-mentioned neutralization step is performed on pre-SAP (polymer which will, upon neutralization, become SAP) after the pre-SAP has already been admixed with fiber in a web and the degree of neutralization is kept partial, preferably under about 80 mol %, then other steps for the manufacture of the resultant SAP may be according to any of the prior art techniques for making SAPs. For example, the SAP may be manufactured by any of the well known solvent polymerization techniques or may be manufactured by any of the well known inverse suspension or emulsion polymerization techniques, discussed above.

Accordingly, olefinically unsaturated carboxylic and/or sulfonic acid-group-containing monomers may be polymerized to manufacture the SAPs, typically in an amount of at least about 10%, more preferably about 25%, and even more preferably about 55 weight % to about 99.9 weight %. Representative acid groups include, but are not limited to, acrylic acids, methacrylic acids, 2-acrylamidol-2-methylpropane sulfonic acid, and mixtures thereof. Also, the acid groups are present as salts, such as sodium salt, potassium salt, or ammonium salt.

Various other monomers that are useful in the manufacture of the SAPs include, but are not limited to, acrylamide, methacrylamide, maleic acid, maleic anhydride, esters (such as hydroxyethyl acrylate, hydroxyethylmethacrylate, hydroxypropylmethacrylate, glycidylmethacrylate, and dimethyl-aminoalkyl-methacrylate), dimethylaminopropyl-acrylamide, and acrylamidopropyl trimethyl-ammonium chloride, typically in amounts ranging from above 0 weight % up to about 60 weight %. Percentages above 60 weight % of these monomers usually have an undesirable effect of deteriorating the swelling capacity of the resultant SAP, and hence, percentages below about 60 weight % of these monomers are most desired.

Preferably, the monomers employed are water insoluble. Also preferably, the resultant SAPs are water insoluble.

The acid groups of the SAPs should be partially neutralized to at least about 25 mol %. More particularly, the degree of neutralization should be to at least about 50 mol %. Even more particularly, the preferred SAP comprises cross-linked acrylic acid or methacrylic acid, that has been neutralized to a degree ranging from about 50 mol % to about 80 mol %.

For the partial neutralization that is performed in situ, the neutralizing agent may be any suitable organic or inorganic base that is soluble in water. Examples of bases include, but are not limited to, sodium hydroxide, potassium hydroxide, lithium hydroxide, ammonium hydroxide, ammonia, sodium carbonate, potassium carbonate, and mixtures thereof. Additionally, neutralization may be effected with a neutralizing agent chosen from organic amines, including, but not limited to, ethanolamine, diethanolamine, triethanolamine, methyl diethanolamine, butyldiethanolamine, diethylamine, dimethylamine, trimethylamine, triethylamine, tributylamine, and mixtures thereof. Combinations of bases and amines may be employed. A very suitable base for use as a neutralizing agent in the present invention is sodium carbonate.

Various network X-linking agents are useful in the manufacture of the SAPs, and the agents should have (1) at least two ethylenically unsaturated double bonds, (2) one ethylenically unsaturated double bond and one functional groups reactive toward acid groups, or (3) several functional groups reactive toward acid groups. Various types of suitable network X-linking agents include, but are not limited to, acrylate and methacrylate of polyols (such as butanedioldiacrylate, hexanedioldimethacrylate, polyglycoldiacrylate, trimethylalpropanetriacrylate, tetrahydrofurfuryl-2-methacrylate, glycerol dimethacrylate, allyloxy polyethylene glycol methacrylate, and ethoxylated trimethylalpropanetriacrylate), allylacrylate, diallylacrylamide, triallylamine, diallylether, methylenebisacrylamide, glycerol dimethacrylate, N,N-diethylaminoethyl methacrylate, N-dimethylaminopropyl methacrylamide, N-methylol methacrylamide, and N-methylalacrylamide. These network X-linking agents are distinguished from and not to be confused with the surface X-linking agents discussed below.

No specific limitations exist vis-a-vis the shape of the particles of the SAPs, and likewise, no specific limitations exist vis-a-vis the shape of the particles of the pre-SAPs. Accordingly, the particles may be in the form of irregularly shaped particles, in the form of small spheres, and combinations thereof. A typical particle size distribution ranges from about 20 to about 2,000 micrometers, preferably from about 40 to about 900 micrometers, and more preferably from about 60 to about 850 micrometers.

However, as is well-known, particle sizes of about 30 micrometers and larger are the sizes generally employed for a wet-laid process. Thus, since the inventive web of SAP together with fiber is made by a wet-laid process, particle sizes under about 30 micrometers are generally undesired.

During the wet-laid process, the weight ratio of the polymer component to the fibrous component is controlled to be in a range from about 90:10 to about 5:95. A very suitable polymer:fiber ratio is from about 30:70 to about 40:60, more preferably about 35:65.

Although comminuted wood pulp (i.e., cellulosic fiber, colloquially referred to as fluff) is preferred for the fibrous component of the web for the present invention, other wettable fibers such as cotton linters may be used. Furthermore, meltblown synthetic fibers such as polyethylene, polypropylene, polyesters, copolymers of polyesters and polyamides, and the like, may be employed. The fibrous component may also be formed from a mixture of wood pulp fluff and one or more such meltblown fibers. For example, the fibrous component may comprise at least about 5 weight %, preferably about 10 weight % synthetic polymer fibers, and the remainder may comprise wood pulp fluff. The fibers of the web are generally hydrophilic or rendered hydrophilic through a surface treatment. Cellulosic fiber is preferred, and a preferred one is sold by Georgia Pacific under the trademark GOLDEN ISLES® 4800.

More particularly, the inventive web of SAP together with fiber (made by a wet-laid process involving partial in situ neutralization of pre-SAP mixed with fiber) exhibits a CRC property that is far superior to that of the prior art web of SAP together with fiber (made by a wet-laid process involving total in situ neutralization of pre-SAP mixed with fiber) as disclosed in the above-discussed U.S. Pat. No. 4,270,977.

The inventive web will typically have a CRC above about 10 g/g, often above about 11 g/g, with the SAP component of the web contributing above about 25 g/g, often above about 27 g/g. On the other hand, the prior art totally in situ neutralized web (as per the above-noted U.S. Pat. No.4,270,977) will typically have a CRC below about 7 g/g, often below about 6 g/g, with the SAP component of the web contributing below about 20 g/g, often below about 19 gig. Thus, the inventive webs exhibit a superior CRC property as compared to those webs disclosed in the above-discussed U.S. Pat. No. 4,270,977.

Moreover, as is known from the above-mentioned U.S. Pat. No. 5,409,771, providing a coating of a surface X-linking agent onto particles and then heating the coated particles to effect surface X-linking improves the AUL property. As is well known, in general, non-surface X-linked SAPs typically display an AUL (performed at 0.3 psi, which is about 20 g/cm$^2$) ranging from about 6 to about 14 g/g, whereas surface X-linked SAPs typically display an AUL (performed at 0.3 psi, which is about 20 g/cm$^2$) above at least about 13 g/g, often above about 14 g/g.

Therefore, a surface X-linking treatment optionally may be performed for the webs of the present invention. Treatment is preferably performed at some point during the wet-laid method of the present invention so that the resultant SAP in the web of SAP and fiber is surface X-linked.

Regardless of whether a surface X-linking treatment has or has not been performed in the present invention, the web will typically have an AUL (performed at 0.3 psi, which is about 20 g/cm$^2$) above about 13 g/g, often above about 14 g/g, with the SAP component of the web contributing above about 30 g/g, often above about 32 g/g. On the other hand, the totally in situ neutralized web of the prior art (which is not surface X-linked as per U.S. Pat. No. 4,270,977) will typically have an AUL below about 10 g/g, often below about 9 g/.g, with the SAP component of the web contributing below about 19 g/g, often below about 18 g/g.

Thus, the inventive webs exhibit a superior AUL property as compared to those webs disclosed in the above-discussed U.S. Pat. No. 4,270,977.

As described in the above-mentioned U.S. Pat. No. 5,409,771, for coating of particles with a surface X-linking agent, the particles may be mixed with an aqueous-alcoholic solution of an alkylene carbonate surface X-linking agent. Various alcohols, such as methanol, ethanol, butanol, butyl glycol, and mixtures thereof, may be employed. Typically, the water is present in an amount of 0.3 to 5.0% by weight, relative to the particles. However, the alkylene carbonate surface X-linking agent may be dissolved in water, without the presence of any alcohol. Additionally, the alkylene carbonate surface X-linking agent may be applied from a powder mixture, for instance, with an inorganic carrier material, such as $SiO_2$. The alkylene carbonate is distributed evenly on the particles by employing a mixer, such as a fluidized bed mixture, a paddle mixer, a milling roll, or a twin-worm-mixer. The coating of the particles with the surface X-linking agent also may be carried out during any of the process steps during the manufacture of the particles. In the present invention, a very suitable alkylene carbonate is ethylene carbonate.

Although the preferred intended use of the inventive web is as a core composite in a disposable sanitary article, such as a diaper, an adult incontinence garment, a sanitary napkin, or a bandage, the inventive web may be employed in various other end products. For instance, the web can be useful in filtration, such as for removal of water or moisture from gasoline, fuel, oil, organic solvent, and the like. Additionally, the web may be useful as an absorbent liner in food packaging, and depending on the particular polymer in accordance with the regulations of the U.S. Food and Drug Administration, may or may not be able to be in direct contact with the food. Furthermore, the web may be used to make a backing tape useful as a water absorbent to be placed together with fiber optic strands inside of a protective sheath. There are may other uses, and it is not intended to be limited to any of the specific uses recited here.

As set out in the Laboratory Examples below, in order to characterize both the webs and the SAP component of these webs (both those of the present invention, as well as those that are comparisons), the centrifuge retention capacity (CRC) property and the absorbency under load (AUL) property were measured in the following manner.

CRC Property. Retention of an aqueous 0.9 weight % NaCl solution was determined according to the tea bag test method and reported as an average value of two measurements. Approximately 200 mg of particles, that had been sieved to a particle size distribution ranging from 300 to 600 micrometers, were enclosed in a tea bag and immersed in the 0.9 weight % NaCl for 30 minutes. Next, the tea bag was centrifuged at 1600 rpm for 3 minutes and weighed. The diameter of the centrifuge apparatus was about 18 mm. Two tea bags without particles were used as blanks.

Then, the CRC property (measured in grams of liquid absorbed per gram of particles) was calculated according to the following equation.

$$CRC = (W_3 - W_2 - W_1)/W_1$$

where:

CRC=retention after 30 minutes immersion time $W_1$=initial weight in grams of particles $W_2$=average weight in grams of two blanks after centrifugation $W_3$=weight in grams of test tea bag after centrifugation AUL Property. The absorbency by the particles of an aqueous 0.9 weight % NaCl solution under load was determined according to the method described on page 7 of the above-mentioned published European Patent Application No. 0 339461 A1. The pressure loads were, respectively, 20 g/cm$^2$ (which is about 0.3 psi) or 60 g/cm$^2$ (which is about 0.9 psi).

An initial weight of approximately 160 mg of particles, which had been sieved to a particle size distribution from 300 to 600 micrometers, was placed in a cylinder with a sieve bottom, and loaded by a piston exerting a pressure load of 0.3 or 0.9 psi.

The cylinder was subsequently placed on a Demand-Absorbency-Tester on a glass fritted disk of 125 mm diameter, then covered by a Whatman Filter Paper #3. Next, the particles were allowed to absorb the NaCl solution for 1 hour. After the 1 hour, the swollen particles were re-weighed, and the grams of NaCl solution that had been retained were calculated. The AUL of the particles was the grams retained.

LABORATORY EXAMPLES

In the following examples, each SAP was a sodium polyacrylate made by solvent polymerization. Also, each percentage recited was a weight %, unless specifically designated otherwise as a mol %.

EXAMPLE 1

In Situ Neutralization of Mixture of Pre-SAP with Fiber to Form Web of SAP with Fiber

EXAMPLE A

Web with 70 mol % Neutralization

Acrylic acid in an amount of 40.0% was mixed with 0.06% EO-TMPTA, 0.06% All-PEGMA, and 1.00% of an aqueous solution containing 0.0248% ferrous sulfate as an initiator component. EO-TMPTA and All-PEGMA are both X-linking agents. The mixture was then diluted with 56.34% water.

An aliquot of 3898.4 grams of the resultant diluted monomer solution was then cooled to about 2 to 5° C. Next, the solution was purged with nitrogen while maintaining it at 2 to 5° C. for 30 minutes.

To the resultant, the following were added in sequence: (a) 1.29% of an aqueous solution containing 0.54% hydrogen peroxide and 1.55% sodium persulfate and (b) 1.25% of an aqueous solution containing 0.32% sodium erythobate. The sodium erythobate forms a redox initiator couple with the hydrogen peroxide. The sodium persulfate is a thermal initiator. Polymerization started immediately and was carried out for 25 minutes in the absence of stirring.

The resultant polymer gel was then ground using a meat grinder, followed by drying at 130° C. for 45 minutes. The resultant dried polymer (which was a pre-SAP) was pulverized into particulate polymer with a particle size distribution ranging from 90 micrometers to 850 micrometers.

Next, 0.80 gram of the pulverized pre-SAP, 1.48 grams of cellulosic fiber (sold under the trademark GOLDEN ISLES® 4800 by Georgia Pacific), and 200 grams of tap water was mixed to form a slurry. The resultant slurry was then poured into a laboratory web molder having a 150 micrometer polyester screen at the bottom. The web molder was made with a stainless steel, sampling chamber on the top for retaining the slurry. The chamber measured 8.5 cm in diameter and 10 cm in height. Also, the web molder had a bottom section that was connected through a ball valve to a vacuum system. After the slurry had been agitated with a 3-blade, fan-shaped, turbine agitator moving in an up-and-down fashion for approximately 30 seconds, water was vacuum-drained from the slurry at approximately 60 mm Hg of vacuum.

Then, for the in situ neutralization, 5% aqueous sodium carbonate solution was added to obtain a calculated degree of neutralization of 70 mol % based on the polymer acid groups. The neutralized wet web of SAP with. cellulosic fiber was then dried in an oven at 130° C. for 30 minutes. In order to run the CRC tests and AUL tests, the dried web was cut with a cutting die into pieces having a diameter of 2 inches (2.54 cm).

EXAMPLE B

Web with 70 mol % Neutralization

The procedure of Example A was repeated, except for the following. After the pre-SAP had been dried and pulverized into particles having a particle size distribution ranging from 90 micrometers to 850 micrometers, and prior to the in situ neutralization step, a surface X-linking procedure was conducted.

More specifically, the dried pulverized particles were sprayed with 2.5%, based on the weight of the dried polymer, of an aqueous solution containing 40% ethylene carbonate and 20% polyethylene glycol (molecular weight=300) in order to form on the particles a coating of ethylene carbonate surface X-linking agent. Then, the coated polymer was heated for 45 minutes at 150° C. prior to cooling and then sieving.

Next, in the same manner as described in Example A, in situ neutralization to a degree of 70 mol % was performed, and followed by drying and then cutting the resultant dried neutralized web into pieces having a diameter of 2 inches (2.54 cm) in order to perform the CRC tests and AUL tests.

EXAMPLE C

Web with 70 mol % Neutralization

The procedure of Example B was repeated, except for the following. The aqueous, surface X-linking solution was sprayed at 3%, based on the weight of the dry polymer, and contained 33.3% ethylene carbonate and 33.3% polyethylene glycol (molecular weight=300). Dried neutralized web was cut into pieces of 2 inch (2.54 cm) diameter for the CRC tests and AUL tests.

COMPARISON EXAMPLE D

Web with 100 mol % Neutralization

This comparison example was intended to repeat the in situ total neutralization process of pre-SAP with cellulosic fiber to form the resultant web of SAP with cellulosic fiber, as disclosed in the above-mentioned U.S. Pat. No. 4,270,977.

More specifically, a pre-SAP that was a co-polymer of methylacrylate and methacrylic acid (with a molar ratio of 65/35 of methylacrylate to methyacrylic acid)-was prepared according to the procedure described in PART A of EXAMPLE 1 in column 14 of U.S. Pat. No. 4,270,977.

Next, the procedure described above in Example A in order to achieve in situ neutralization was repeated, except that instead was employed a 2% aqueous sodium hydroxide solution to obtain a calculated degree of neutralization of 100 mol % based on the acid groups of the co-polymer. As in example A, the neutralized wet web was then dried, followed by cutting into pieces having a diameter of 2 inches (2.54 cm) in order to conduct CRC tests and AUL tests.

COMPARISON EXAMPLE E

Web with 110 mol % Neutralization

The procedure of Comparison Example D was repeated, except that the in situ neutralization was carried out so that the resultant degree of neutralization was 110 mol %. Neutralized dry web was cut into pieces of 2 inch (2.54 cm) diameter for the CRC tests and AUL tests.

The 2 inch (2.54 cm) diameter pieces of webs from Examples A, B, and C, and from Comparison Examples D and E were tested, and the results are summarized below in Table 1.

TABLE 1

CRC Tests and AUL Tests for Web of SAP/Cellulosic Fiber

| Example | Polymer/ Fiber Ratio | mol % Neutr. based on acid in polymer | CRC of Web (g/g) | CRC (SAP contribution) (g/g) | 0.3 psi AUL of Web (g/g) | 0.3 psi AUL (polymer contribution) (g/g) |
|---|---|---|---|---|---|---|
| None | 0/100 | 0 | 2.3 | n.a. | 4.3 | n.a. |
| Example A | 35/65 | 70 | 13.5 | 34.3 | 15.1 | 35.2 |
| Example B | 35/65 | 70 | 11.6 | 28.9 | 14.7 | 34.0 |
| Example C | 35/65 | 70 | 11.0 | 27.1 | 14.1 | 32.3 |
| Comparison D | 35/65 | 100 | 5.4 | 11.2 | 8.9 | 17.4 |
| Comparison E | 35/65 | 110 | 5.8 | 12.3 | 9.4 | 18.9 |

CRC (of Web) = 0.65 CRC (of Fiber) + 0.35 CRC (of SAP);
AUL (of Web) = 0.65 AUL (of Fiber) + 0.35 AUL (of SAP).

EXAMPLE 2

Neutralization of Mixture of Pre-SAP to form SAP, Without Fiber

The following samples of SAPs (but without the presence of any cellulosic fiber), as reported below in Examples A through 1, were made in accordance with the present invention in that each was 70 mol % neutralized, and also the following comparison samples of SAPs (but without the presence of any cellulosic fiber), as reported below in Comparison Examples J and K, were made in accordance with U.S. Pat. No. 4,270,977 in that each was totally neutralized (100 mol % and 110 mol %, respectively). All percentages are weight %, unless specifically designated as mol %.

EXAMPLE A

Acrylic acid in an amount of 40.0% was mixed with 0.08% All-PEGMA as a X-linking agent and 1.00% of an aqueous solution containing 0.0248% ferrous sulfate as an initiator. Next, the mixture was diluted with 56.38% water.

An aliquot of 1461.9 grams of the resultant diluted monomer solution was cooled to about 2 to 5° C., followed by purging with nitrogen while maintaining the solution for 30 minutes at 2 to 5° C.

The following were added in sequence to the resultant: (a) 1.29% of an aqueous solution containing 0.54% hydrogen peroxide and 1.55% sodium persulfate and (b) 1.25% of an aqueous solution containing 0.32% sodium erythobate. The sodium erythobate formed a redox initiator couple with the hydrogen peroxide. The sodium persulfate was a thermal initiator which generates free radicals throughout the course of the reaction to complete the polymerization.

The resultant solution contained the following concentrations of ingredients:

| Ingredients | Weight % |
|---|---|
| Acrylic Acid | 40.0 |
| All-PEGMA | 0.08 |
| Ferrous Sulfate | 0.000248 |
| Hydrogen Peroxide | 0.007 |
| Sodium Persulfate | 0.02 |
| Sodium Erythobate | 0.004 |

-continued

| Ingredients | Weight % |
|---|---|
| Water | 59.88875 |
| TOTAL | 100.00 |

Polymerization started immediately after the addition of the initiators, and was continued for 25 minutes in the absence stirring.

The resultant polymer gel was then ground using a meat grinder, followed by drying at 130° C. for 45 minutes. The dried polymer was then pulverized into particulate with a particle size distribution ranging from 90 to 850 micrometers.

Next, 10 grams of the dry particulate pre-SAP was mixed with 25.8 grams of 20% aqueous sodium carbonate solution in order to obtain a degree of neutralization of 70 mol % of the carboxylic acid groups. The resultant neutralized polymer, which was now a SAP, was dried at 130° C. for 2 hours, followed by sieving to a particle size distribution ranging from 150 to 840 micrometers in order to perform the CRC tests and AUL tests.

EXAMPLE B

Acrylic acid in an amount of 40.0% was mixed with 0.06% EO-TMPTA, 0.06% All-PEGMA, and 1.00% of an aqueous solution containing 0.0248% ferrous sulfate as an initiator component. EO-TMPTA and All-PEGMA are both X-linking agents. The mixture was then diluted with 56.34% water.

An aliquot of 3898.4 grams of the resultant diluted monomer solution was then cooled to about 2 to 5° C. Next, the solution was purged with nitrogen while maintaining it at 2 to 5° C. for 30 minutes.

To the resultant, the following were added in sequence: (a) 1.29% of an aqueous solution containing 0.54% hydrogen peroxide and 1.55% sodium persulfate and (b) 1.25% of an aqueous solution containing 0.32% sodium erythobate. The sodium erythobate forms a redox initiator couple with the hydrogen peroxide. The sodium persulfate is a thermal initiator. Polymerization started immediately and was carried out for 25 minutes in the absence of stirring.

The resultant polymer gel was then ground using a meat grinder, followed by drying at 130° C. for45 minutes. The resultant dried polymer (which was a pre-SAP) was pulverized into particulate polymer with a particle size distribution ranging from 90 micrometers to 850 micrometers.

Next, 10 grams of dry particulate pre-SAP was mixed with 25.8 grams of 20% aqueous sodium carbonate solution to obtain a degree of neutralization of 70 mol % of the carboxylic acid groups. The resultant neutralized polymer, which was now a SAP, was dried at 130° C. for 2 hours, followed by sieving to a particle size distribution ranging from 150 to 840 micrometers in order to perform the CRC tests and AUL tests.

EXAMPLE C

The same procedure as in Example A was repeated except that 0.12% of EO-TMPTA was employed as a X-linking agent instead of 0.08% All-PEGMA.

EXAMPLE D

The procedure of Example B was repeated, except that the monomer concentration of acrylic acid was 31.0%, and both EO-TMPTA and All-PEGMA were employed as X-linking agents, each in an amount of 0.0465%.

EXAMPLE E

The procedure of Example B was repeated, except that the following surface X-linking treatment was conducted prior to conducting the neutralization with aqueous sodium carbonate.

More specifically, the particulate dry pre-SAP was sprayed with 3%, based on the weight of the dry polymer, of an aqueous solution containing 10% ethylene carbonate surface X-linking agent in order to provide a coating of this surface X-linking agent on the particles. The coated polymer was then heated for 20 minutes at 180° C., cooled, and sieved to a particle size distribution ranging from 90 micrometers to 850 micrometers.

EXAMPLE F

The procedure of Example E was repeated, except that the sprayed aqueous solution contained 50% ethylene carbonate, and then the coated polymer was heated for 180 minutes at 110° C.

EXAMPLE G

The procedure of Example E was repeated, except that the spraying was with 2% (instead of 3%) of the aqueous ethylene carbonate solution, and the solution contained 30% (instead of 10%) ethylene carbonate. Also, the heating of the polymer particles coated with ethylene carbonate was conducted for 60 minutes at 150° C. (instead of 20 minutes at 180° C.).

EXAMPLE H

The procedure of Example G was repeated, except that the spraying was with 2.5%. Also, the aqueous solution contained 40% ethylene carbonate, and additionally, 20% polyethylene glycol (molecular weight=300).

EXAMPLE I

The procedure of Example H was repeated, except that the spraying with the aqueous solution was with 3%, based on the dry polymer, and the aqueous solution contained 33.3% ethylene carbonate and 33.3% polyethylene glycol (molecular weight=300).

COMPARISON EXAMPLE J

The purpose of this example was to repeat the procedure disclosed in the above-mentioned U.S. Pat. No.4,270,977 for making totally neutralized SAP (but without any cellulosic fiber present).

More specifically, a pre-SAP, which was a co-polymer of methylacrylate and methacrylic acid (with a molar ratio of 65/35 of methylacrylate to methacrylic acid), was prepared according to the procedure described in PART A of EXAMPLE 1 in column 14 of U.S. Pat. No. 4,270,977.

Then, 10 grams of the dry pre-SAP having a particle size distribution ranging from 90 micrometers to 850 micrometers was totally neutralized with 32.6 grams of a solution of 5% aqueous caustic soda in order to obtain a degree of neutralization of 100 mol % of carboxylic acid groups. The resultant neutralized SAP was then dried for 2 hours at 130° C., followed by sieving to a particle size distribution ranging from 150 micrometers to 840 micrometers in order to perform the CRC tests and AUL tests.

COMPARISON EXAMPLE K

The procedure of Comparison Example J was repeated, except that the neutralization was with 35.8 grams of the aqueous solution of 5% caustic soda in order to obtain a degree of neutralization of 110 mol % of carboxylic acid groups.

The various SAPs from Examples A through I and the comparison SAPs from Comparison Examples J and K were tested for CRC and AUL. The results are summarized in Table 2 below.

TABLE 2

| Example | Degree of Neutralization (mol %) | CRC (g/g) | 0.3 psi AUL (g/g) | 0.9 psi AUL (g/g) |
|---|---|---|---|---|
| Example A | 70 | 45.6 | — | — |
| Example B | 70 | 37.5 | 9.7 | — |
| Example C | 70 | 33.4 | — | — |
| Example D | 70 | 42.3 | — | — |

TABLE 2-continued

| Example | Degree of Neutralization (mol %) | CRC (g/g) | 0.3 psi AUL (g/g) | 0.9 psi AUL (g/g) |
|---|---|---|---|---|
| Example E | 70 | 31.0 | 22.4 | 8.2 |
| Example F | 70 | 33.3 | 21.0 | 8.3 |
| Example G | 70 | 30.8 | 27.9 | 10.8 |
| Example H | 70 | 28.9 | 28.0 | 13.0 |
| Example I | 70 | 26.8 | 28.2 | 20.1 |
| Comparison J | 100 | 10.0 | 12.9 | 11.0 |
| Comparison K | 110 | 10.6 | 11.7 | 10.5 |

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for improving the centrifuge retention capacity property of an in situ wet-laid water sorptive product, said method comprising:
   (a) forming an aqueous suspension comprising a slurry of
      (i) a potentially water swellable polymer component; and
      (ii) a fibrous component; wherein the weight ratio of said polymer component to said fibrous component is controlled to be in a range from about 90: 10 to about 5: 95;
   (b) forming a composite product from said suspension;
   (c) contacting said composite product with an amount of an aqueous solution of a neutralizing agent sufficient to achieve a partial degree of neutralization of the acid groups of the polymer component of said composite product; and
   (d) drying said neutralized composite product to achieve a water sorptive product of superaborbent polymer component with fibrous component, said water sorptive product having improved centrifuge retention capacity properties.

2. The method of claim 1, wherein the potentially water swellable polymer component comprises the reaction product of:
   (a) an olefinically-unsaturated acid selected from the group consisting of carboxylic acid, sulfonic acid, and mixtures thereof;
   (b) a compatible co-monomer for the acid of (a); and
   (c) a cross-linking agent; said reaction product
      (i) being water insoluble and
      (ii) having carboxyl groups present therein, which carboxyl groups, when neutralized to their salt form, maintain the polymer as water insoluble and convert the polymer component into a superabsorbent polymer component.

3. The method of claim 1, wherein the partial neutralization in step (3) is less than about 80 mol %.

4. The method of claim 1, wherein the neutralizing agent in step (3) is selected from the group consisting of bases, amines, and combinations thereof.

5. The method of claim 1, further including a surface cross-linking treatment.

6. The method of claim 1, wherein the water sorptive product has a centrifuge retention capacity property above about 10 grams/gram.

7. The method of claim 1, wherein the water sorptive product has an absorbency under load property above about 13 grams/gram at about 20 grams/cm$^2$ (about 0.3 psi).

8. A method for making a water sorptive product using a wet-lay process comprising the steps of:
   (a) mixing a pre-superabsorbent polymer and a fiber; and
   (b) partially neutralizing the pre-superabsorbent polymer after the mixing of the pre-superabsorbent polymer with the fiber during the wet-laid process of making a web, thereby making the water sorptive product exhibiting a superior centrifuge retention capacity property.

9. The method of claim 8, wherein the partially neutralizing of the pre-superabsorbent polymer comprises to a degree of neutralization less than about 80 mol %.

10. The method of claim 8, wherein the pre-superabsorbent polymer comprises a reaction product of:
    (a) an olefinically-unsaturated acid selected from the group consisting of a carboxylic acid, a sulfonic acid, and mixtures thereof;
    (b) a compatible co-monomer for the acid of (a); and
    (c) a cross-linking agent; said reaction product
       (i) being water insoluble and
       (ii) having carboxyl groups present therein, which carboxyl groups, when neutralized to their salt form, maintain the polymer as water insoluble and convert the polymer component into a superabsorbent polymer component.

11. The method of claim 8, further comprising the step of surface cross-linking the neutralized pre-superabsorbent polymer.

12. The method of claim 8, wherein the water sorptive product has a centrifuge retention capacity property above 10 grams/gram.

13. The water sorptive product of claim 8, wherein the water sorptive product has an absorbency under load property above about 13 grams/gram at about 20 grams/cm$^2$ (about 0.3 psi).

* * * * *

UNITED STATES PATENT AND TRADEMARK OFFICE
CERTIFICATE OF CORRECTION

PATENT NO. : 7,144,980 B2
APPLICATION NO. : 11/052331
DATED : December 5, 2006
INVENTOR(S) : Fang Sun et al.

Page 1 of 1

It is certified that error appears in the above-identified patent and that said Letters Patent is hereby corrected as shown below:

Column 1,
Line 13, "situneu-" should read -- situ neu- --.

Column 5,
Line 31, "19 gig." should read -- 19 g/g. --.

Column 8,
Line 4, "with." should read -- with --.

Column 8,
Line 60, "acid)-was" should read -- acid) was --.

Signed and Sealed this

Twenty-ninth Day of May, 2007

JON W. DUDAS
*Director of the United States Patent and Trademark Office*